United States Patent
Rines

(10) Patent No.: US 7,178,530 B2
(45) Date of Patent: Feb. 20, 2007

(54) METHOD OF AMELIORATING VISION-INHIBITING EFFECTS OF CATARACTS AND THE LIKE

(76) Inventor: Robert H. Rines, 13 Spaulding St., Concord, NH (US) 03301

( * ) Notice: Subject to any disclaimer, the term of this patent is extended or adjusted under 35 U.S.C. 154(b) by 526 days.

(21) Appl. No.: 10/283,009

(22) Filed: Oct. 25, 2002

(65) Prior Publication Data

US 2004/0082882 A1    Apr. 29, 2004

(51) Int. Cl.
*A61B 19/00* (2006.01)

(52) U.S. Cl. ..................................... 128/898

(58) Field of Classification Search ................ 128/898; 606/4, 6; 604/20, 22
See application file for complete search history.

*Primary Examiner*—Corrine McDermott
*Assistant Examiner*—William Matthews
(74) *Attorney, Agent, or Firm*—Rines and Rines

(57) ABSTRACT

A technique and apparatus for ameliorating, at least temporarily, vision-inhibiting effects of cataracts and the like within the lens of an eye, wherein MHz high-frequency ultrasound of relatively low power much less than that which would cause rupturing or fragmentation of the lens is used to treat the eye and for limited irradiation periods sufficient, however, to agitate and move around protein clumps or the like within the lens that cause the cataracts.

Figure 1:
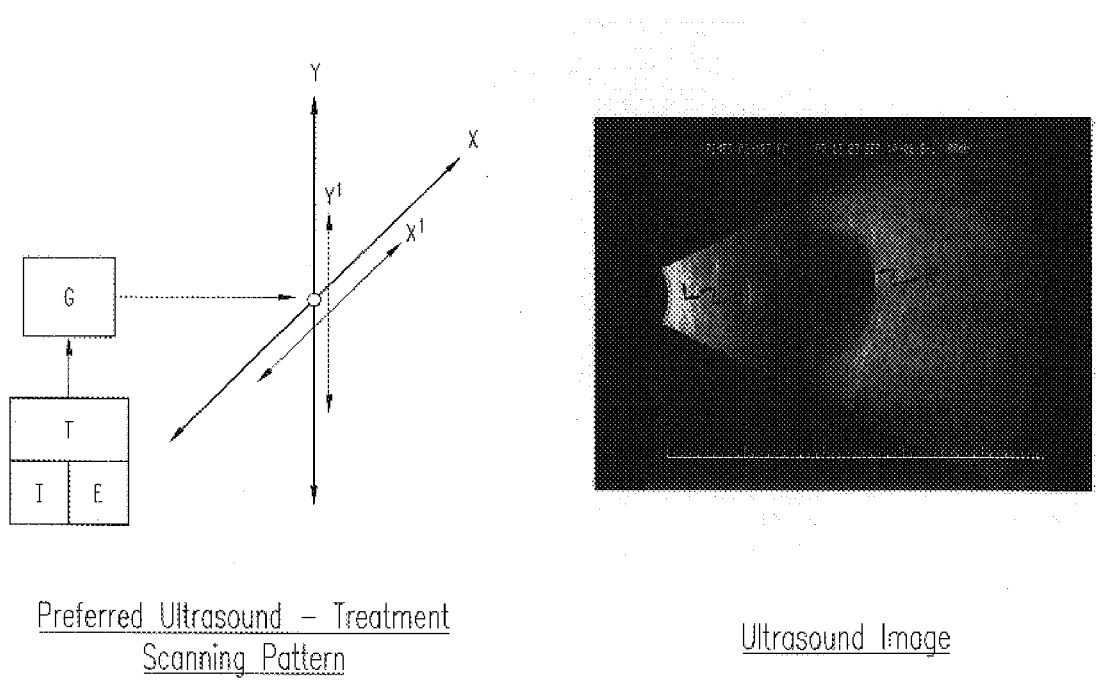

23 Claims, 1 Drawing Sheet
(1 of 1 Drawing Sheet(s) Filed in Color)

Preferred Ultrasound – Treatment Scanning Pattern

Ultrasound Image

METHOD OF AMELIORATING VISION-INHIBITING EFFECTS OF CATARACTS AND THE LIKE

FIELD

The present invention relates to the vision-inhibiting effects of the development of cataracts in the lenses of eyes, and more particularly, to the apparent discovery of techniques for ameliorating at least some of the vision-inhibiting effects of cataracts developed in the lenses of eyes (blurriness, "water-fall" misting, cloudiness, bright-light glare, particularly at night or in artificially lighted places, clarity reduction, "haloing" around the lights, etc.) through a novel and critical use of relatively low power, relatively high-frequency ultrasound irradiation and scanning "treatment" of the lenses in situ in the eyes.

BACKGROUND

Acoustic energy sources of a wide range of frequencies and power have been copiously used during the past century for a myriad of applications ranging from communication, industrial surface cleaning and even jack-hammering (U.S. Pat. Nos. 3,969,984 and 4,166,507—Bouyoucus), underwater sonar echo ranging and acoustic scan imaging (U.S. Pat. No. 2,258,725—Rines), and medical diagnostic treatment and internal body examination ("sonogram"), and, with, particular reference to the eyes, pulverizing of lenses with cataracts for removal and replacement by an artificial generally plastic interocular lens (IOL), [U.S. Pat. No. 3,589,363—Banko and Kelman; *Phaco-emulsification Surgery*, Devine et al, Permagon Press 1991, pp. 1–5; U.S. Pat. No. 3,526,219—Balamith, and U.S. Pat. No. 3,857,387—Shock; Cavitron/Kelman Model 6500, etc.; Bausch & Lomb Storz Millenium Model; H. M. Clayman et al, *J. Cataract Refract Surg.*, Vol. 12, March 1986, pp 158–161].

Ultrasonic cleaners and therapeutic and surgical ultrasound (phacoemulsification of cataractous lenses, lithotripay of kidney stones, sports injuries as to knees, shoulders, etc.) use relatively high power and relatively low ultrasound frequencies and generate heat in tissues.

The cataract is a clouding of the lens of the eye lying behind the eye iris and pupil, causing hazy or blurring vision as the lens focuses light onto the retina in back of the eye. In the normal lens, the water and protein therein serve to provide a clear lens. During aging (and for other causes, also), some proteins apparently clump together, clouding areas of the lens—forming commonly near the center of the lens ("nuclear"); but cataracts also form in the lens peripheral cortex region and spoke therefrom inwardly toward the center ("cortical"); and in other instances, as in the case of some diabetes, a so-called "subcapsular" cataract forms at the back of the lens.

The relatively high power or intensity of therapeutic lower-frequency ultrasound injected internally of the eye by the phacoemulsification instrument tip inserted into the small incision made in the front of the capsule holding the natural lens, phacoemulsifies the cataracted lens and, in effect, particularlizingly dissolves or emulsifies the same so that the particles or fragments may be gently vacuum-removed from the eye.

In connection with the phacoemulsification applications, ultra (or super-) sound impulses, generally in the relatively low ultrasonic frequency range of about 30 to 80 kHz at power levels of about 20 watts, more or less, are used, generating strokes of between about 1 to 4 mils (acceleration of up to the order of 125,000 grams), hammering, shattering and fragmenting microchips to emulsify into a suspension. A small incision is first made into the cornea next to the sclera into which a phacoemulsification ultrasound probe is introduced, ultrasonically to break up, rupture and fragment and emulsify the cloudy lens into tiny particles or pieces which can be removed through the top of the probe by the before-mentioned vacuuming of the fragments, so as then to permit subsequent introduction or implantation of an appropriate substitute artificial IOL.

Once it has been decided thus to surgically remove a cataracted lens, it is then necessary to measure the patient's specific internal eye axial and other dimensions as by echoing low power ultrasound pulses from the surfaces of the anterior cornea, anterior lens, posterior lens retina and scelera, and displaying the same, and making needed calculations for replacing the lens with an intraocular lens. Appropriately, such an ultrasound "measurement" of the eye is generally effected by probing the eyeball with an ultrasound probe for generally less than or of the order of a minute or so, and with relatively low power pulses (compared to those use for phacoemulsification) and of relatively high ultrasound frequency of about 10 MHz, more or less. Such "diagnostic" ultrasound pulses in the megahertz range and of relatively low power do not generate any substantial heat in tissue and have been safely used for such imaging measurements, not for therapeutic usages, and with total safety to the eye and its components. The type $I^3$ SYSTEM A B Diagnostics ophthalmic ultrasound instrument of Innovation Imaging Inc. of Sacramento, Calif., for example, is widely used for such entirely safe eye measurement and imaging purposes. This enables determining, including imaging (approximately 25 cps repetition rate), the particular internal eye shape, lens position, and multi-dimensional and axial distances to the retina, etc., displaying the same on real-time pulse-echo displacement vs. time displays (A-type presentation) as the operator traverses with the probe, and/or converting the resulting echo digital signals into images, as with an oscillating transducer that enables also B-type presentation, as in the accompanying FIG. 1, where the lens (L) and retina (R) acoustic images of one of applicant's eyes is displayed. This is more fully described, for example, in the 1995 $I^3$ SYSTEM—ABD manual of said Innovation Imaging Inc.

Underlying the present invention, however, is a serendipitous apparent discovery that by irradiating the eye by slowly scanning such a relatively low power relatively high frequency ultrasound probe beam over the closed eyeball lid and irradiating through a water-containing interfacing transparent cup over the open-lid eye, or contacting the open eye on a film of liquid de-sensitizing drops and/or of ultrasound coupling gel or the like, and for much longer periods than the minute or so of brief usual probing for obtaining eye-structure dimensional measurements, some of the pre-existing vision-inhibiting effects, as before described, appear to be rapidly and radically ameliorated.

SUMMARY

In summary, the invention embraces a method of ameliorating, at least temporarily, impaired vision effects in an eye lens in which protein clumping has produced a cataract, that comprises, applying an irradiation treatment of a relatively high-frequency ultrasound energy beam externally against the front of the eye and scanning the same along and over substantially the complete front surface thereof; adjusting the intensity of the energy to a power range well below that which would cause rupturing and fragmenting of the lens, but sufficient at least to cause substantial protein clump agitation, movement, and thinning within the lens; and limiting the treatment to a time period sufficient to cause substantial agitation movement.

Preferred and best mode implementations are later detailed.

DRAWINGS

The patent or application file contains at least one drawings shown in a photograph form.

Copies of this patent or patent application publication with color drawing(s) will be provided by the Office upon request and payment of the necessary fee.

The invention will now be described with reference to FIG. 1 showing a photographic reproduction of an actual ultrasound image of the interior of an eye with a preferred ultrasound-treatment scanning pattern apparatus schematically illustrated to the left.

PREFERRED EMBODIMENTS

In initial experiments, within a few hours of such pulse irradiation at said 10 MHz frequency, for several minutes—a time period relatively long compared to the measurement tests—say about 10 minutes or so—and, preferably with about equal times for closed-lid and then open-eye scanning irradiation as above-described and as later more fully detailed, a remarkable improvement in vision clarity was observed—including well-focused and sharply clear nightlight-environment vision, totally void of blurriness and halos. This clarity continued throughout the next weeks and thereafter for longer times. This followed an earlier "measurement" instrument irradiation for about 1½ minutes with de-sensitizing open eye coupling gel—contacting of the ultrasound A type probe.

While it is not necessary fully to understand all the reasons for this observed distinct ameliorating of the previous vision blurriness and other impairment before discussed, it being sufficient to describe the conditions found necessary to produce the effect in practice, it may be that this extended period(s) of high-frequency low-power ultra-sound irradiation "treatment" (also as contrasted with the just a minute or so of relatively short probe dimensional measurements), starts agitating movement, thinning, perhaps even shrinking or evaporating, or even disintegrating the occluding and clouding protein particle clumps or areas within the lens, thereby freeing areas of the lens for clearer light transmission.

The wavelength of ultrasound in the liquid of the lens, for the before-mentioned exemplary frequency of 10 MHz, as an illustration, assuming a lens liquid velocity of about 1550m/sec is about 0.155 mm, which appears to be comparable to or even smaller than some protein clumps forming the cataracts—the nominal thickness of the lens itself being of the order of about 1.5 mm ("Accurate Ultrasonic Biometry in Pseudophakia", Holladay J. T. et al, *American Journal of Ophthalmology*, April, 1993, p.538). Undoubtedly standing (reflected) and traveling waves and resonances are set up within the lens— longitudinal, transverse and mixed mode types, (see for example, U.S. Pat. No. 2,622,470 of R. H. Rines) which disturb and substantially agitate protein aggregates and possibly dissipate or shear the clouding and/or, at the very least, mechanically move and displace or re-arrange their positions within the lens.

Though at this time it is not known if long-term periodic repetition of such ultrasound irradiation "treatment" of the lens can result in permanent elimination or permanent reduction of the deleterious effects of the clouding material within the sealed lens in situ, nor are optimum frequencies or probe repetition rates or probe powers or treatment repetition periods and times as yet known, the invention, even in its present preliminary and rudimentary state is still believed to be of great utility as at least for the temporary relief of occluded vision for patients suffering from such vision impairment and its accompanying debilitating effects, and who have not yet taken or been able to take (as in the case of some diabetics and others) the surgical permanent course of seeking implants.

For the purposes of the invention, preferably the ultrasound beam is a pulsed pencil beam of frequency ranging from a few MHz (order of about 3) to the order of the before-mentioned ten or tens of megahertz frequency, and of about fractional or a few watts of average low power or so, and is scanned manually by its probe handling and/or is scanned by internal oscillating of the probe crystal, as under motor control, generating the scanning ultrasound beam, and over the total front of the eye; though wider beams and even continuous-wave or frequency-swept or phase-modulated ultrasound may be used for thus irradiating the eye. The ultrasound energy irradiation "treatment", however, should extend over the complete scanned three-dimensional curve along substantially the complete front surface of the eye, as before explained, as through scanning the closed lid and/or through a water or saline or gel liquid layer along the total front of the open eye. At present, the precise maximum length of time of treatment with total safety for the eye and its inner components is not fully known; but periodic irradiation over about five to ten minutes has been safely used, and has been found to be efficacious for the purposes of the invention as will now be detailed. In FIG. 1, this is schematically illustrated to the left of the acoustic eye image as a pattern represented by the overall scan arrows x and y of the ultrasound probe P (with the before-mentioned internal probe oscillating scanning $x^1$–$y^1$ therewithin, if used) the probe being excited from the preferably pulsed ultrasound generator G controlled by a timer T both for successive interval application control I and an overall total time exposure control E.

In the treatments above-described, two patient eyes were each ultrasonically irradiated with pulsed 10 MHz low power ultrasound radiation applied in successive periodic bursts or intervals of about 15–25 seconds, each, and of low power range, as before discussed—totally inadequate and well below the power required to rupture or fragment the lens or to generate any substantial heat in the tissue—and as follows:

| | Eye No. 1 | Eye No. 2 |
|---|---|---|
| Scanning | | |
| 1. Through lid, scanned therealong from end to end and top to bottom. | Total treatment of about 4+ minutes | Total treatment of about 2½+ minutes |
| 2. Then through saline water layer in an eye-inserted | Total treatment of about 5+ minutes | Total treatment of about 3+ minutes |

-continued

| | Eye No. 1 | Eye No. 2 |
|---|---|---|
| transparent cup applied to the open eye and under the lids. | | |
| Visual Acuity Results | | |
| | Before treatment-haze around night lights; still indistinct with corrective glasses: OD 20/70 | Before treatment-haze around night lights; misty or indistinct distance vision even with corrective glasses: OS 20/40 |
| | After treatment-clarity significantly improved. Night-light vision clear-no halos, From one week to over a month later, still no halos or haze and continued improved clarity OD 20/50 | After treatment-clarity significantly improved. Night-light vision crisp, no halos. From one week to over a month later, continued clarity improvement; no halos or haze. OS 20/30 |

A second substantially identical irradiation treatment was repeated a week later with the following results:

| Continued improved clarity-no halos or haze. | Continued improved clarity-no halos or haze. |
|---|---|

While, as before stated, further refinement and more copious clinical trials are indicated, even the initial state of the invention has great utility as at least for the rapid temporary relief of occluded vision and its debilitating effects.

Based upon the discovery, this technique may well be used for preventing the development of a serious problem of clumping—both as a prophylaxis or preventative as during routine eye examinations, and as an inhibitor of the onset of, or preliminary clumping. The low-power of this high frequency treatment has fortuitously been found to produce no harmful effects, including no substantial tissue heating within the eye structure and no other stressing or damage to such structure; and the limiting of the total time of the radiation exposure—just sufficient to develop substantial agitation—can insure total safety as earlier discussed.

Further modifications will also occur to those skilled in this art and such are considered to fall within the spirit and scope of the invention as defined in the appended claims.

What is claimed is:

1. A method of ameliorating, at least temporarily, impaired vision effects in an eye lens in which protein clumping has produced a cataract, that comprises, applying an irradiation treatment of a relatively high-frequency ultrasound energy beam externally against the front of the eye and scanning the same along and over substantially the complete front surface thereof; adjusting the intensity of the energy to a power range well below that which would cause rupturing and fragmenting of the lens, but sufficient at least to cause substantial protein clump agitation, movement, or thinning within the lens; and limiting the treatment to a time period longer than about a minute and selected from the group consisting of about 2½, 3, 4, 5 and 10 minutes sufficient to cause substantial agitation movement.

2. The method of claim 1 wherein the ultrasound energy is in the MHz frequency range.

3. The method of claim 2 wherein said range extends from a few MHz up to the order of 10 MHz and higher.

4. The method of claim 3 wherein the average power range is of the order of fractional to a few watts.

5. The method of claim 3 wherein said ultrasound energy is pulsed.

6. The method of claim 5 wherein the energy is pulsed at a repetition rate of the order of about 25/second.

7. The method of claim 5 wherein the pulsing comprises frequency sweeping.

8. The method of claim 3 wherein said scanning is effected manually and/or by oscillating the beam.

9. The method of claim 5 wherein said total treatment exposure time period is of the order of substantially ten minutes, more or less.

10. The method of claim 9 wherein the ultrasound is applied in successive intervals during said total treatment exposure.

11. The method of claim 1 wherein the treatment is periodically repeated.

12. The method of claim 11 where the periodicity of the treatment is over weeks.

13. A method for ameliorating, at least temporarily, vision-inhibiting effects of cataracts within the lens of an eye, that comprises, radiating the eye with MHz high-frequency ultrasound of relatively low power much less than that which would cause rupturing or fragmentation of the lens, and limiting the irradiation periods to longer than about a minute and selected from the group consisting of about 2½, 3, 4, 5 and 10 minutes and to be sufficient only to agitate and move around protein clumps within the lens that cause cataracts.

14. The method of claim 13 wherein said power is adjusted to a low value that avoids any substantial generation of heat in the lens or eye.

15. The method of claim 13 wherein said radiating is effected while scanning along and over substantially the complete front surface of the eye.

16. A method for preventing the development of vision-inhibiting effects of protein clumping within the lens of an eye, that comprises, radiating the eye with MHz high-frequency ultrasound of relatively low power much less than a higher power which would cause rupturing or fragmentation of the lens; and, during either or both of routine eye examination or upon the onset of initial protein clumping, limiting the radiation periods to longer than about a minute and selected from the group consisting of about 2½, 3, 4, 5 and 10 minutes to be sufficient to create ultrasound-wave agitation within the lens to inhibit protein clumping therewithin.

17. A method of ameliorating, at least temporarily, impaired vision effects in an eye lens in which protein clumping has produced a cataract, that comprises, applying an irradiation treatment of a relatively high-frequency ultrasound energy beam externally against the front of the eye and scanning the same along and over substantially the complete front surface thereof; adjusting the intensity of the energy to a power range well below that which would cause rupturing and fragmenting of the lens, but sufficient at least to cause substantial protein clump agitation, movement, or thinning within the lens; and limiting the treatment to a time period longer than a minute and sufficient to cause substantial agitation movement during such scanning over the three-dimensional curve of the complete front surface of the eye.

18. A method of ameliorating, at least temporarily, impaired vision effects in an eye lens in which protein clumping has produced or is producing a cataract, that comprises, applying an irradiation treatment of a relatively high-frequency ultrasound energy beam externally against the front of the eye and scanning the same along and over substantially the complete front curve of the front surface of the eye; adjusting the intensity of the energy to a power range well below that which would cause rupturing and fragmenting of the lens, but sufficient at least to cause substantial protein clump agitation, movement, or thinning within the lens; and Limiting the treatment to a time period sufficient to cause substantial agitation movement during such scanning over the complete front surface of the lens.

19. The method of claim 18 wherein the ultrasound energy application is pulsed during said scanning.

20. The method of claim 18 wherein the ultrasound energy is applied in successive intervals during the scanning treatment.

21. The method of claim 18 wherein the treatment time is about 2½ minutes.

22. The method of claim 18 wherein the ultrasound energy is in the MHz frequency range.

23. The method of claim 22 wherein said range extends from a few MHz up to the order of 10 MHZ and higher.

* * * * *